(12) United States Patent
Roe

(10) Patent No.: US 7,063,731 B2
(45) Date of Patent: Jun. 20, 2006

(54) METHOD AND APPARATUS FOR DETECTING PARTICLES IN A GAS FLOW

(75) Inventor: Morris Anthony Roe, Robertson (AU)

(73) Assignee: Goyen Controls Co. Pty Ltd, Milperra (AU)

( * ) Notice: Subject to any disclaimer, the term of this patent is extended or adjusted under 35 U.S.C. 154(b) by 0 days.

(21) Appl. No.: 10/271,096

(22) Filed: Oct. 11, 2002

(65) Prior Publication Data

US 2003/0089159 A1 May 15, 2003

Related U.S. Application Data

(63) Continuation of application No. PCT/AU01/00417, filed on Apr. 11, 2000.

(51) Int. Cl.
*G01N 37/00* (2006.01)

(52) U.S. Cl. ..................................... 95/28.04; 73/28.01

(58) Field of Classification Search ............... 73/28.01, 73/28.04, 28.05, 28.02; 324/454
See application file for complete search history.

(56) References Cited

U.S. PATENT DOCUMENTS

| | | | |
|---|---|---|---|
| 4,117,715 A | 10/1978 | Hoenig | |
| 4,179,934 A | 12/1979 | Svarovsky | |
| 4,531,402 A | 7/1985 | Reif | ............................... 73/28 |
| 4,607,228 A | 8/1986 | Reif | ........................... 324/454 |
| 4,631,482 A | 12/1986 | Newton | |
| 4,656,832 A * | 4/1987 | Yukihisa et al. | ............... 60/303 |
| 4,904,944 A | 2/1990 | Dechene | |
| 5,095,275 A | 3/1992 | Dechene | |
| 5,448,172 A | 9/1995 | Dechene | |
| 5,591,895 A | 1/1997 | Rigby | |
| 5,644,241 A | 7/1997 | Hewelt | |

FOREIGN PATENT DOCUMENTS

| | | |
|---|---|---|
| DE | 28 54 657 A1 | 10/1979 |
| WO | WO 94/23281 | 10/1994 |
| WO | WO 99/05479 | 2/1999 |
| WO | WO 99/50641 | 10/1999 |

* cited by examiner

*Primary Examiner*—Daniel S. Larkin

(57) ABSTRACT

The application discloses several methods of detecting particles moving in a gas flow, a detection means (70), a method of improving the linearity of the signal produced by a triboelectric particle detector, a method to test a signal path of an emission monitor, an emission monitor for detecting particles, and a method of detecting faults in a triboelectric probe of system for detecting particles entrained in a gas flow. The particle detection means (70) includes a gas flow deflection means (40) having an upstream face (43) and a downstream face (45) and a detector (42, 44) associated exclusively with the downstream face (45). Deflecting the gas flow creates vortices that have little effect on the large particles, but cause the small particles to move close to the detectors on the downstream face. Therefore the downstream detectors (42, 44) are particularly sensitive to light particles. The method improves of small particles and provides accurate particle counts.

9 Claims, 11 Drawing Sheets

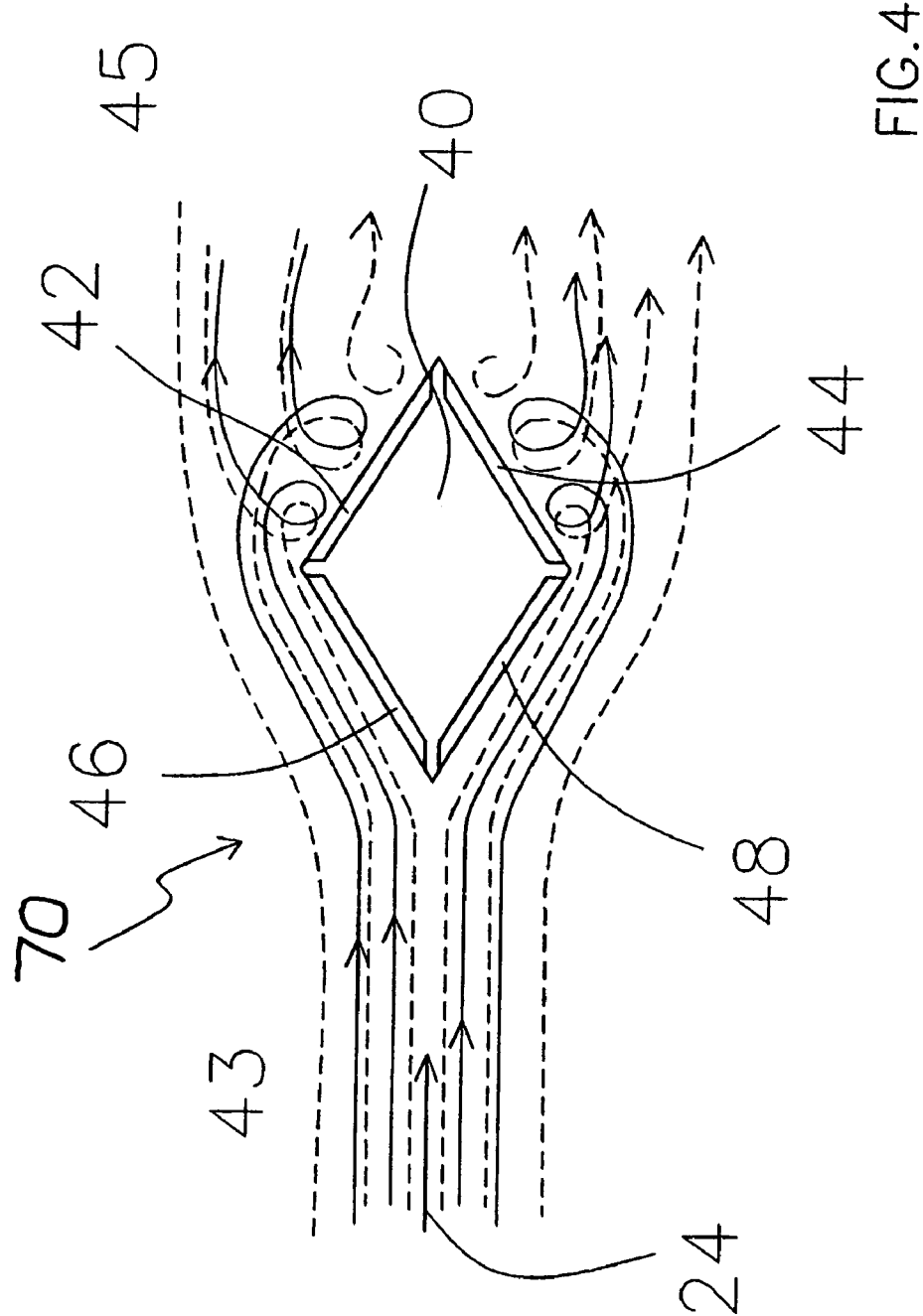

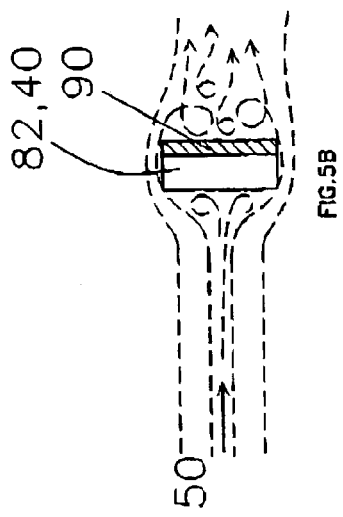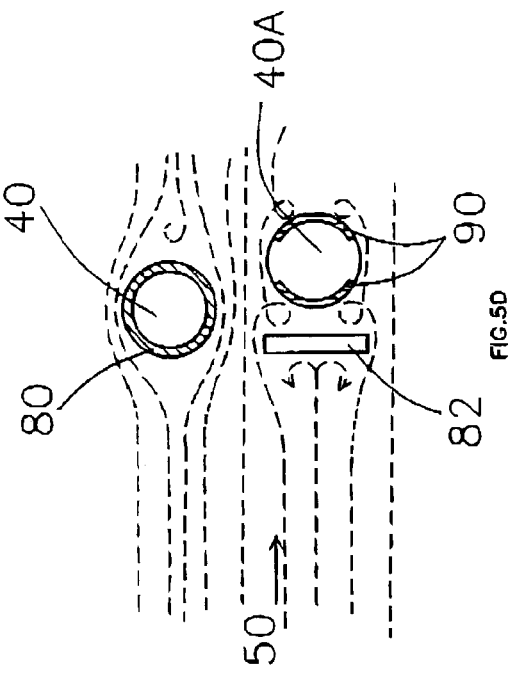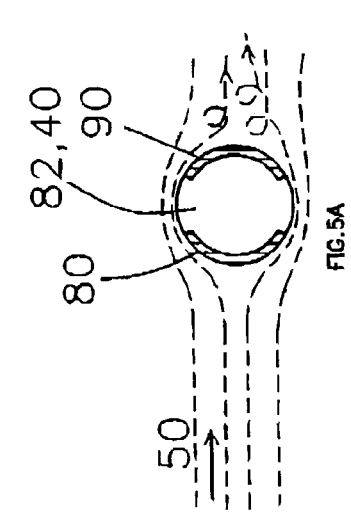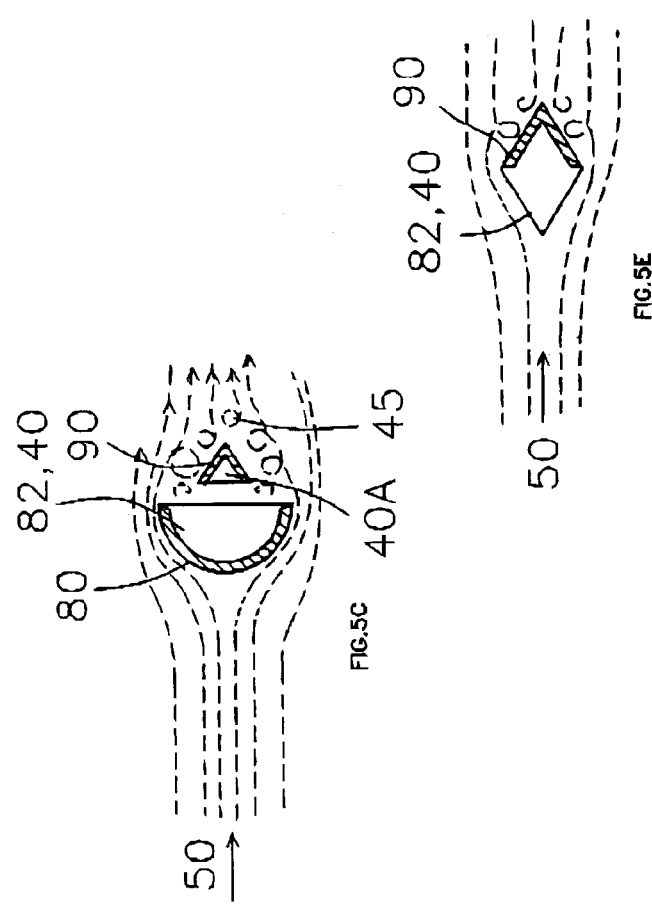

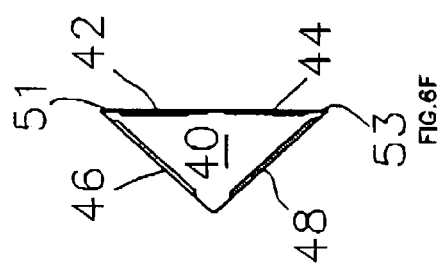
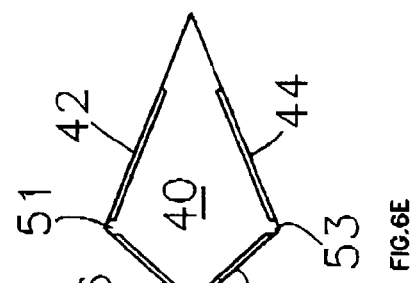
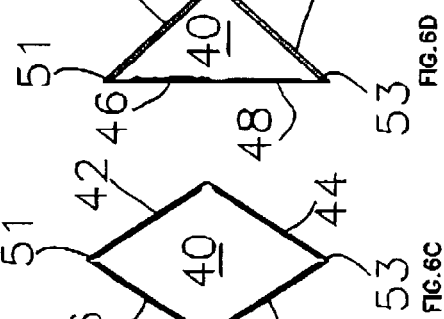
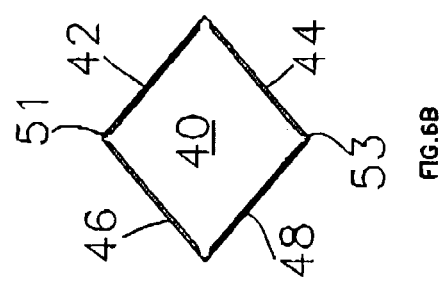
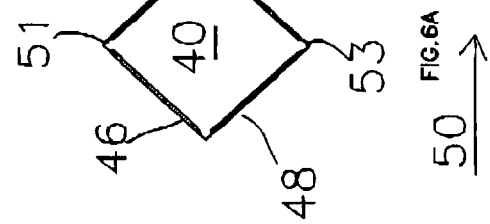
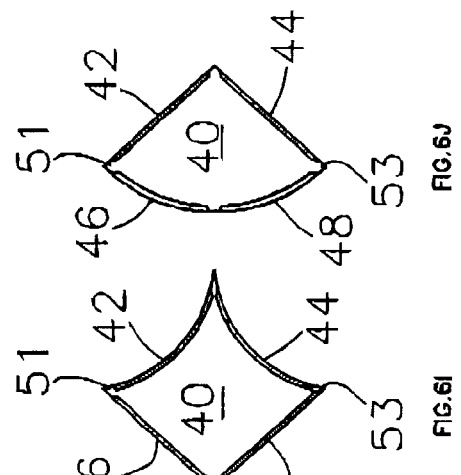
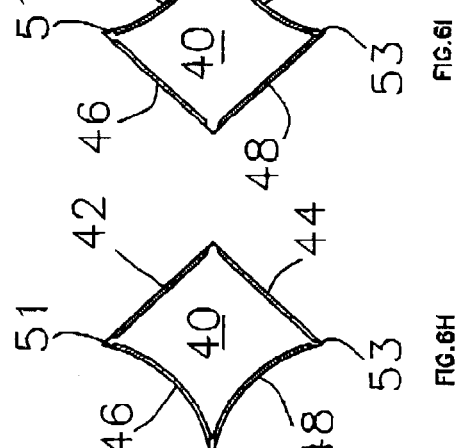
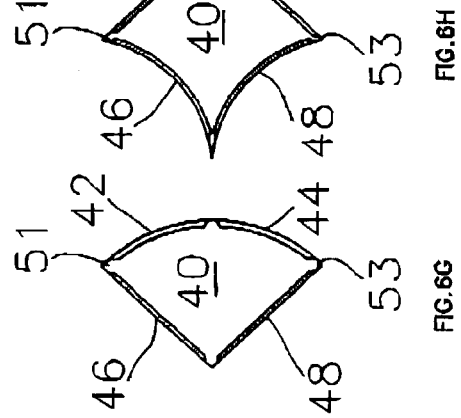

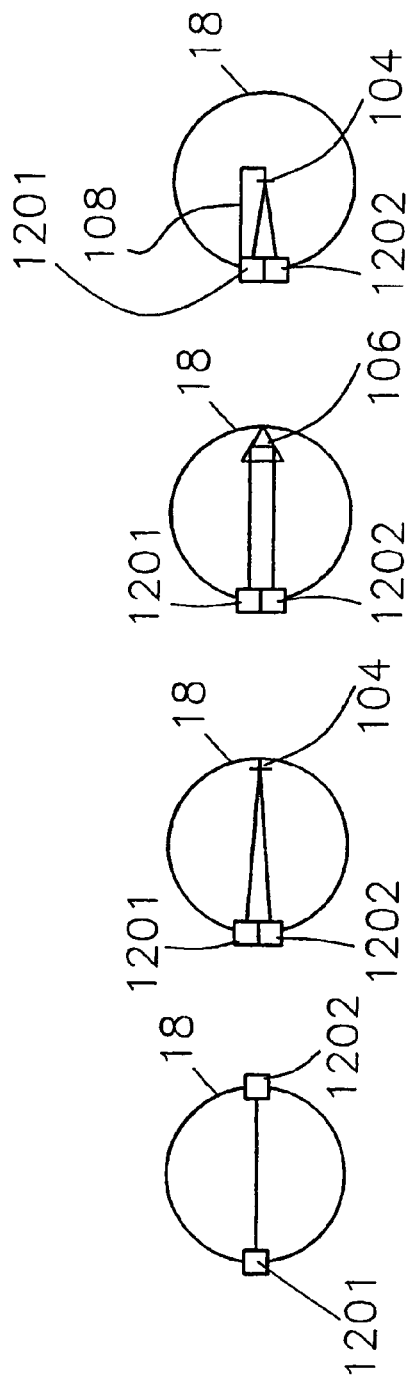
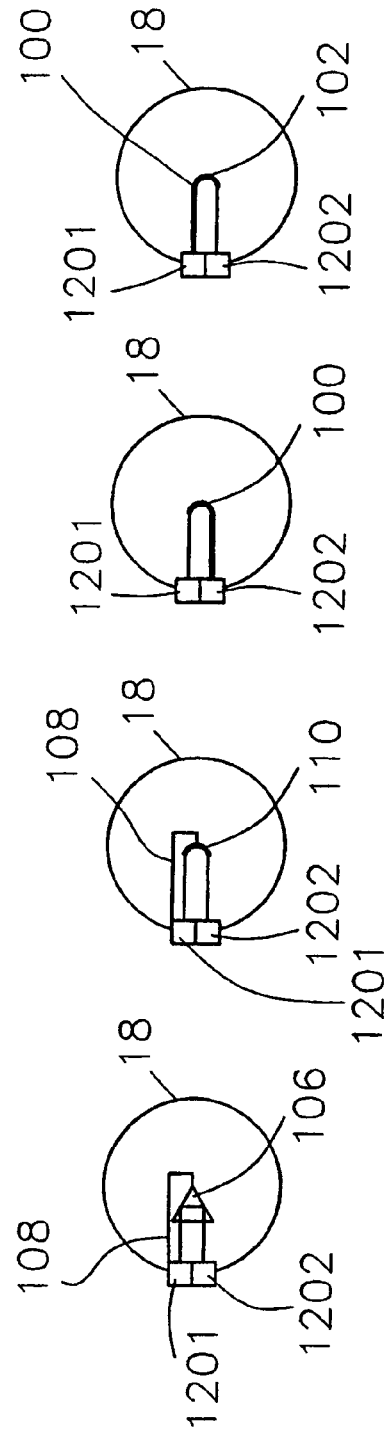
FIG. 10 PRIOR ART

METHOD AND APPARATUS FOR DETECTING PARTICLES IN A GAS FLOW

This Application is a continuation of International Application PCT/AU01/00417 filed 11 Apr. 2000 and Applicant specifically claims priority from said International Application.

FIELD OF THE INVENTION

The invention relates to a method and apparatus for detecting particles entrained in a gas flow and to an apparatus capable of carrying out such a method. More particularly, the invention relates to a triboelectric emission monitor and an optical dynamic emission monitor.

BACKGROUND OF THE INVENTION

There are several known means of measuring the level of particulate material entrained in a gas flow. These can be split into a number of categories including those based on electrostatic or triboelectric phenomena on the one hand, and those based on optical phenomena on the other.

As will be appreciated by a person skilled in the art, known particulate emission monitors have various drawbacks, such as, limited sensitivity to light particles, a tendency to have display velocity dependence in their measurements, non linearity between particle concentration and detector signal and limited diagnostic capabilities, to name but a few.

The applicant does not concede that the prior art described herein is part of the common general knowledge at the priority date of the application.

SUMMARY OF THE INVENTION

According to a broad aspect of the invention, there is provided a detection means for detecting particles entrained in a gas stream, said detection means comprising:
 a body adapted to be located in said gas stream and having an upstream face and a downstream face;
 a detector associated with said downstream detection face adapted to detect particles impinging on or passing over said downstream face; and
 said body being shaped and configured to deflect said gas stream around said body in a manner to cause generally turbulent gas flow of said gas stream adjacent said downstream face;
 said detector being adapted to generate a detection signal as a consequence of particles entrained in said turbulent gas flow impinging on or passing over said downstream face.

Preferably the detection signal is used to calculate a detection value that is representative of said particles entrained in said turbulent gas flow.

In one embodiment, the detector may be adapted to detect particles impinging on or passing over said upstream face of said body.

In another embodiment, a further detector adapted to detect particles impinging on or passing over said upstream face of said body.

The at least one detection value may include any one or more of the following detection values for said particles: mass concentration; mass flow rate; numerical concentration; volume concentration; class concentration; or particle size.

The detector may be a triboelectric detector or an optical dynamic opacity detector.

Optionally, the body is substantially symmetrical about a plane which lies parallel to the direction of flow of said gas stream.

According to another aspect of the present invention there is provided a method of detecting particles moving in a gas flow including the steps of
 a) locating a particle detection means in said gas flow to measure particles in a portion of said gas flow to be sampled;
 b) separating out of said portion of said gas flow to be sampled, via a separation means, a substantial number of particles whose presence is not to be detected while causing same to remain in said gas flow;
 c) causing said portion of said gas flow to be sampled to cooperate with said particle detection means to enable particles, which remain in said portion of said gas flow to be sampled, to be detected by said particle detection means.

According to another aspect of the present invention there is provided a method for detecting particles moving in a gas flow including the steps of:
 placing a particle detection means including a gas flow deflection device having an upstream face and a downstream face, and at least one detector associated exclusively with said downstream face, in said gas flow,
 detecting particles flowing in said gas flow as they pass near or over said downstream face.

Preferably said detection means includes at least one detector associated exclusively with said upstream face, and said method additionally includes the step of detecting particles flowing in said gas flow as they pass near or over said upstream face.

Preferably said at least one detector associated exclusively with said downstream face, or said upstream face, additionally detects said particles as they collide with said detection means.

In a preferred embodiment said airflow deflection means, and either one of, said at least one detector associated exclusively with said downstream face, or at least one detector associated exclusively with said upstream face, are combined into a single member.

Preferably one or more of, said at least one detector associated exclusively with said downstream face, or at least one detector associated exclusively with said upstream face, is a triboelectric detector or an optical dynamic opacity detector.

According to another aspect of the present invention there is provided a detection means for detecting a particulate material entrained in a gas flow, said detection means including an upstream face and a downstream face, and at least one detector associated exclusively with said downstream face, wherein, in use said detector associated exclusively with said downstream face detects particles flowing in said gas flow as they pass near or over said downstream face.

Preferably said detection means additionally includes at least one detector associated exclusively with said upstream face wherein, in use said detector associated exclusively with said upstream face detects particles flowing in said gas flow as they pass near or over said upstream face.

Preferably said at least one detector associated exclusively with said downstream face, or said at least one detector associated exclusively with said upstream face, additionally detects said particles as they collide with the detection means.

In one preferred embodiment the airflow deflection means, and either of, said at least one detector associated exclusively with said downstream face, or said at least one detector associated exclusively with said upstream face, are combined into a single member.

Preferably any one or more of, said at least one detector associated exclusively with said downstream face, or at least one detector associated exclusively with said upstream face, is a triboelectric detector and/or optical dynamic opacity detector.

According to another aspect of the present invention there is provided a method of improving the linearity of the signal produced by a triboelectric particle detector including the steps of:

determining the instantaneous number of particles detected by said particle detector;

associating said instantaneous number of particles detected by said particle detector with a value on a characteristic curve;

using said associated value to calculate the particle density from the detected signal.

Preferably the step of calculating the instantaneous number of particles detected by said detection means includes the additional steps of:

determining the numerical density of particles in the gas flow;

estimating the volume over which a particle will be detected by said particle detector;

dividing the numerical density of particles in the gas flow by the volume over which a particle will be detected by said particle detector to obtain the instantaneous number of particles detected by said detection means.

Preferably said characteristic curve is determined empirically for said detection means by a method including the steps of:

maintaining all environmental and internal conditions substantially fixed;

determining a probe current, produced by said detection means at a first known particle density;

varying said particle density in a controlled manner until said particle density is equal to a second known particle density; and while varying said particle density;

determining the probe current for all particle densities between said first and second known particle densities.

Preferably the characteristic curve is substantially a square law for high particle densities.

Additionally it is preferable that the characteristic curve is substantially linear for low particle densities.

According to another aspect of the present invention there is provided a method to test a signal path of an emission monitor for detecting particles entrained in a gas flow, said emission monitor including at least one detector adapted to interact with said particles to produce a detector signal, said detector being coupled to a signal processing means, and said signal processing means being coupled to a measuring means, wherein said signal path is defined as the combination of the signal processing means and a coupling means coupling said detector to said measuring means, said method including the steps of:

applying a validation signal to said signal processing means in addition to said detector signal, thereby defining a combined signal, processing the combined signal using the signal processing means, separating the processed combined signal into a processed detector signal and a processed validation signal, using the processed detector signal to take measurements of the particulate material in the gas flow, comparing the processed validation signal to a predefined control signal in order to detect faults in the signal processing path of said emission measuring means.

Preferably the signal processing means only allows signals within a predetermined pass band to reach said measuring means.

Said validation signal is preferably an AC signal having a frequency within said pass band of said emission monitoring system. Furthermore it is the validation signal is at a frequency of 10 Hz.

Preferably the combined signal is converted to a digital signal, by sampling at a rate of 55 Hz. The processed validation signal can then be filtered from said processed combined signal using a comb filter. In this embodiment preferably the comb filter rejects signals at a frequency of 5 Hz or at one or more harmonics of 5 Hz.

According to another aspect of the present invention there is provided an emission monitor for detecting particles entrained in a gas flow, said emission monitor including at least one detector adapted to generate a detector signal in response to interaction between said detector and said particles, at least one signal processing means, and at least one measuring means, said detector being coupled to a signal processing means, and said signal processing means additionally being coupled to a measuring means, wherein a signal path is defined as the combination of the signal processing means and a coupling means, coupling said detector to said measuring means, said emission monitor further including, signal generating means adapted to produce a validation signal which is additionally coupled to said signal processing means to produce a combined signal at an input of said signal processing means, wherein said combined signal is processed by said signal processing means to produce a processed combined signal, said processed combined signal is separated into a processed detector signal and a processed validation signal, and wherein said measuring means detects particles entrained in the gas flow using said processed detector signal, and additionally compares said processed validation signal with a predetermined control signal to detect faults in said signal processing path.

Preferably said processed validation signal is separated from said processed combined signal using a filter.

The predetermined control signal can be determined by processing a signal identical to said validation signal by applying said signal identical to said validation signal to said signal processing path under a set of control conditions.

Preferably said processing path includes at least one amplifier and at least one low pass filter.

In a preferred embodiment said validation signal is an alternating current. In a particularly preferred embodiment said validation signal has a frequency of 10 Hz.

According to another aspect of the present invention there is provided a method of detecting particles entrained in a gas flow which is substantially independent of the velocity of said particles, using a detection means, including at least one detector, at least one signal processing means and at least one measuring means, said method including the steps of:

placing said detector, in said gas flow such that particles in said gas flow interact with said detector producing a detector signal;

coupling said detector to said signal processing means, said signal processing means adapted to only allow the passage of signals within a predefined frequency pass band to reach said measuring means, said frequency pass band having a central portion, an upper portion and a lower portion, said signal processing means having a frequency response for signals over at least said central portion of said frequency pass band whereby the gain of said signal processing means is inversely proportional to said frequency;

coupling said signal processing means to said measuring means to allow measurement of a processed detector signal.

Preferably for signals over at least said central portion of said pass band the gain of said signal processing means halves if the frequency of said signal doubles.

It is also preferable that the gain of said signal processing means for signals with a frequency above and below said central portion of said frequency pass band, is adjusted to at least partially compensate for the finite width of said frequency pass band.

Preferably the gain of said signal processing means for signals with a frequency above said central portion of said frequency pass band decreases at a lower rate than over said central portion, as frequency increases, and then decreases at a faster rate than over said central portion, and or the gain of said signal processing means for signals with a frequency lower than said central portion of said frequency pass band increases at a greater rate than over said central portion, as frequency falls, and then falls.

According to another aspect of the present invention there is provided a method of detecting particles entered in a gas flow using one detector means, including at least one detector, signal processing means and measuring means, said method being substantially independent of the velocity of said particles, and including the steps of.

placing said detector, in said gas flow such that particles entrained in said gas flow interact electrically with said detector producing a detector signal, said detector signal having a low frequency band centered around a predetermined first frequency and a high frequency band centered on a predetermined second frequency;

coupling said detector to said signal processing means, coupling said signal processing means to a measuring means, wherein said measuring means compares the signal in the high frequency band to the signal in the low frequency band to determine an estimated velocity of said particles based on a predetermined relationship, using said estimated velocity to remove the velocity dependence of the detection of particles entrained in said gas flow.

The relationship is preferably determined empirically.

In a preferred embodiment the ratio of the detector signal in the high frequency band to the detector signal in the low frequency band is used to estimate the velocity of said particles.

In such a method said low frequency band is preferably centered on a frequency of between 0.1 and 2 Hz and/or said high frequency band is centered on a frequency of between 10 and 20 Hz.

In a particularly preferred embodiment said low frequency band is centered on a frequency of 1.0 Hz and/or said high frequency band is centered on a frequency of 12 Hz.

According to another aspect of the present invention there is provided a method of detecting the velocity of particles entrained in a gas flow using a detection means, including at least one detector, signal processing means and measuring means, said method including the steps of:

placing said detector in said gas flow such that particles entrained in said gas flow interact electrically with said detector producing a detector signal, said detector signal having a low frequency band centered around a predetermined first frequency and a high frequency band centered on a predetermined second frequency, coupling said detector to said signal processing means, coupling said signal processing means to a measuring means, wherein said measuring means compares the signal in the high frequency band to the signal in the low frequency band to determine an estimated velocity of said particles based on a predetermined relationship.

Preferably said relationship is determined empirically.

Preferably the detector signal in the high frequency band to the detector signal in the low frequency band is used to estimate the velocity of said particles.

In a preferred embodiment the low frequency band is centered on a frequency of between 0.1 and 2 Hz and/or the high frequency band is centered on a frequency of between 10 and 20 Hz.

In a particularly preferred embodiment said low frequency band is centered on a frequency of 1.0 Hz and/or said high frequency band is centered on a frequency of 12 Hz.

According to another aspect of the present invention there is provided a method of detecting faults in a triboelectric probe of system for detecting particles entrained in a gas flow, said system including at least one probe, signal processing means and measuring means, said probe including at least one electrode electrically exposed to said gas flow and adapted to interact with said particles in said gas flow to produce a probe current, said method including the steps of:

measuring the admittance of the probe;

using either the real or imaginary part, or real and imaginary parts, of the admittance of said probe to detect a fault in the probe.

Preferably the step of measuring the admittance of the probe includes the additional steps of:

applying an admittance measuring signal of a predetermined frequency to said probe through a high impedance circuit;

measuring the vectorial signal at the probe as a result of the application of the admittance measuring signal;

calculating the admittance of the probe based on said vectorial signal.

It is preferable that said real component of said admittance is used to detect a change in conductance of an insulator supporting said probe.

It is also preferable that the imaginary component of said admittance is used to detect a change in the capacitance or susceptance of said probe.

In a preferred embodiment said admittance measurement is performed alternately with particle detection. Alternatively admittance measurement can be performed simultaneously with particle detection.

Preferably said signal processing means includes a means for providing a high probe admittance for signals within a measurement signal pass band and a low probe admittance for signals at the frequency of the admittance measuring signal.

It is preferable that the means for providing a high probe admittance for signals within a measurement signal pass band and a low probe admittance for signals at the frequency of the admittance measuring signal includes an inverting integrator within a frequency independent shunt feedback loop.

In a preferred embodiment the admittance measuring signal is at a frequency of at least 10 kHz.

BRIEF DESCRIPTION OF THE DRAWINGS

A number of embodiments of the present invention will now be described by way of example only, with reference to the accompanying drawings in which:

FIG. 4 is an end view of a probe according to an aspect of the present invention showing air flow around the probe and the mechanism for AC current production for light particle;

FIGS. 5A to 5E shows a series of exemplary probe shapes in accordance with the present invention;

FIGS. 6A to 6J show a further series of exemplary probe cross sectional shapes in accordance with the present invention;

FIGS. 10A to 10H show a number of examples configurations of optical dynamic opacity detectors.

DETAILED DESCRIPTION OF THE EMBODIMENTS

Figure 1:
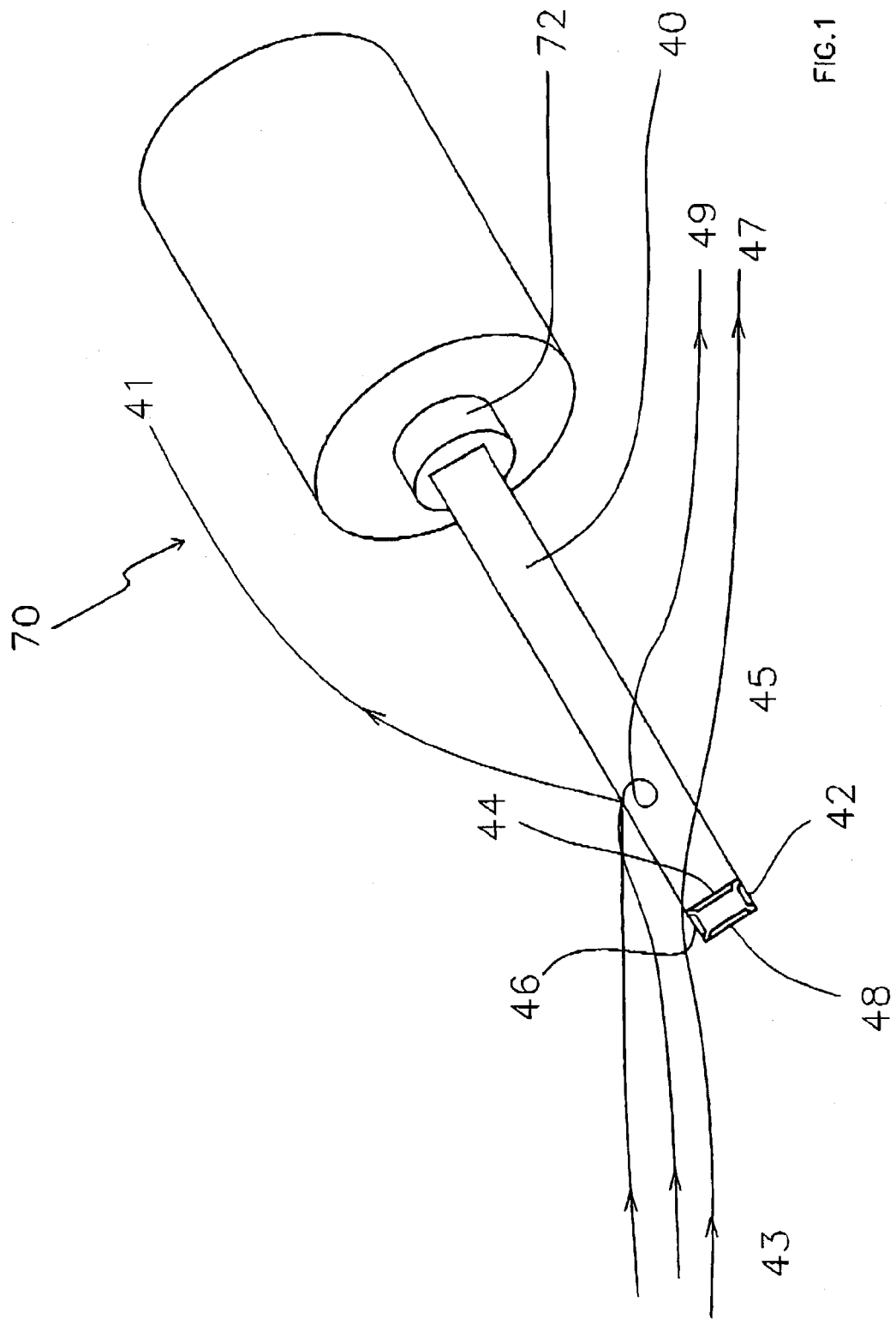
FIG. 1 shows a triboelectric probe according to a preferred embodiment of the present invention.

FIG. 1 illustrates a detection means being an embodiment of the present invention. The detection means 70 is adapted to detect particulate material entrained in a gas flow, the direction of which is indicated by the arrow shown in the streamlines 41, 47, 49. The detection means 70 includes a probe shaft 40 with a generally square cross-section having four faces. On each of the faces of the probe shaft 40 there is a separate and electrically isolated probe electrode 42, 44, 46, 48. Probe electrodes 46 and 48 are located on the upstream side 43 of the probe shaft 40 and probe electrodes 42 and 44 are located on the downstream side 45 of the probe shaft 40. Detection means 70 also includes an insulating sleeve 72 to prevent current leakage from the probe electrodes 42, 44, 46, 48 to a duct (not shown).

When the detection means 70 is placed in a gas flow, particulate material which is suspended in the gas flow interacts with the probe electrodes 42, 44, 46, 48 to produce a signal which can be used to determine the particulate flow rate. Heavy and/or large sized particles interact primarily with the probe electrodes 46, 48 on the upstream side 43 of the probe shaft 40. Whereas lighter and/or smaller particles interact primarily with the probe electrodes 42, 44 on the downstream side 45 of the probe shaft 40. By this means a detector signal will be produced by the upstream electrodes 46, 48, which is related to the quantity of large particles, and a separate signal is produced by the downstream electrodes, 42, 44, which is related to the quantity of small particles in the gas flow. As will be described below, these signals may be processed singly or together to calculate such qualities as:

Mass Concentration;
Mass Flow Rate;
Numerical Concentration:
Volume Concentration; and
Class Concentration.

Additionally, the signals can be processed together to determine the particle size or particles size distribution by empirical methods.

The principle of operation of the detector is as follows.

If the gas flow is smooth then all particles suspended in the gas flow regardless of the particle size follow streamlines in the gas flow. However, if the gas flow is disturbed, for example by placing an object in the gas flow, some particles will continue to move in a straight path (i.e. their inertia will cause them to continue in their original direction as if the disturbance had not occurred), and collide with the obstruction, as depicted by path 41 of FIG. 1, whilst other particles will continue to follow the streamlines of the gas as depicted by path 47 of FIG. 1.

At velocities commonly encountered in bag houses, where a detection means such as described herein may be used, the gas flow will become turbulent on the downstream side 45 of a detector. Tests have shown that the downstream detectors 42, 44 are particularly sensitive to light particles. It is believed that the increased sensitivity of the downstream detectors 42, 44 to light particles is due to the tendency of light particles to be drawn into the turbulent flow downstream of the probe where they circulate back toward the downstream detectors 42, 44 thereby increasing the intensity of the resultant signal generated by the 42, 44. The path 49 is that followed by the lightest particles in the gas flow.

Figure 2:
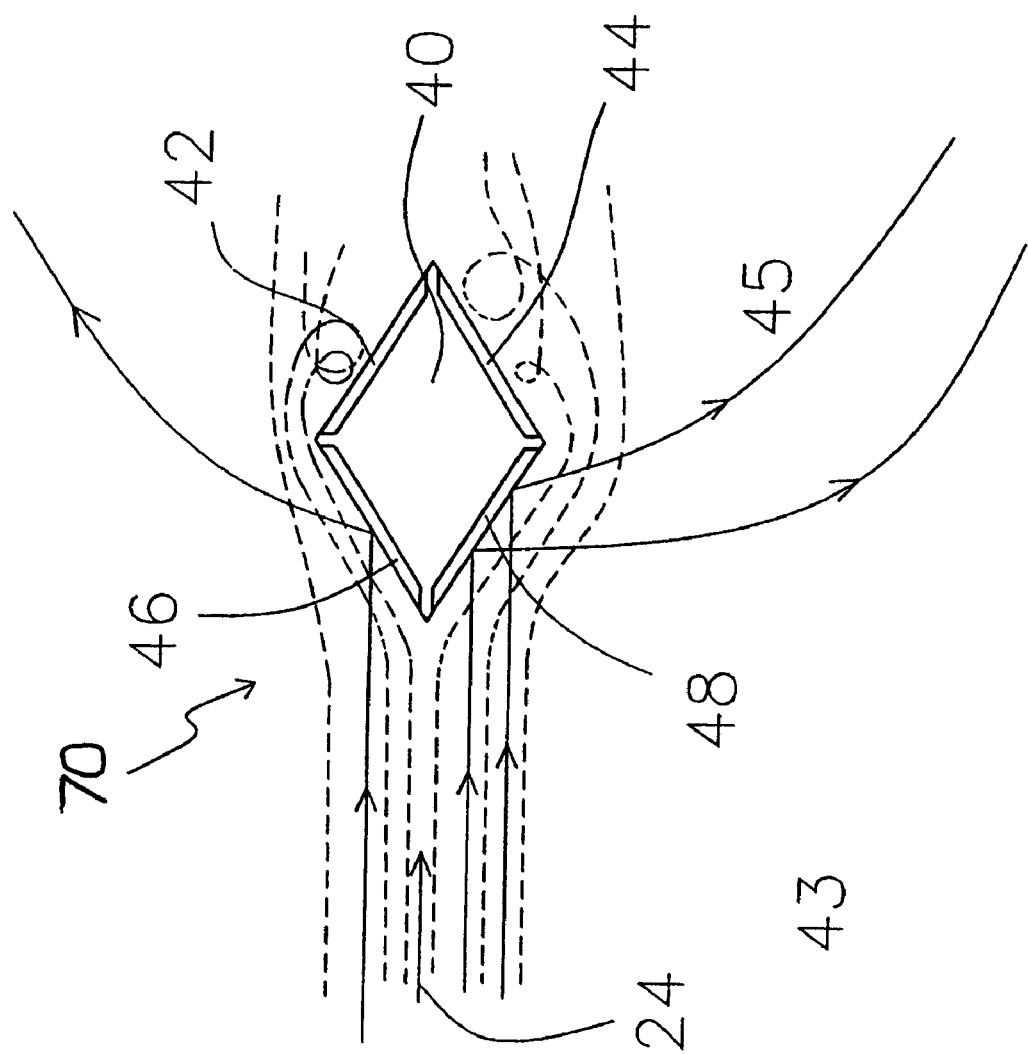
FIG. 2 is an end view of the probe of FIG. 1 showing the air flow around the probe and the mechanism for current production for the heaviest particles (produces both DC and AC current)
Figure 3:
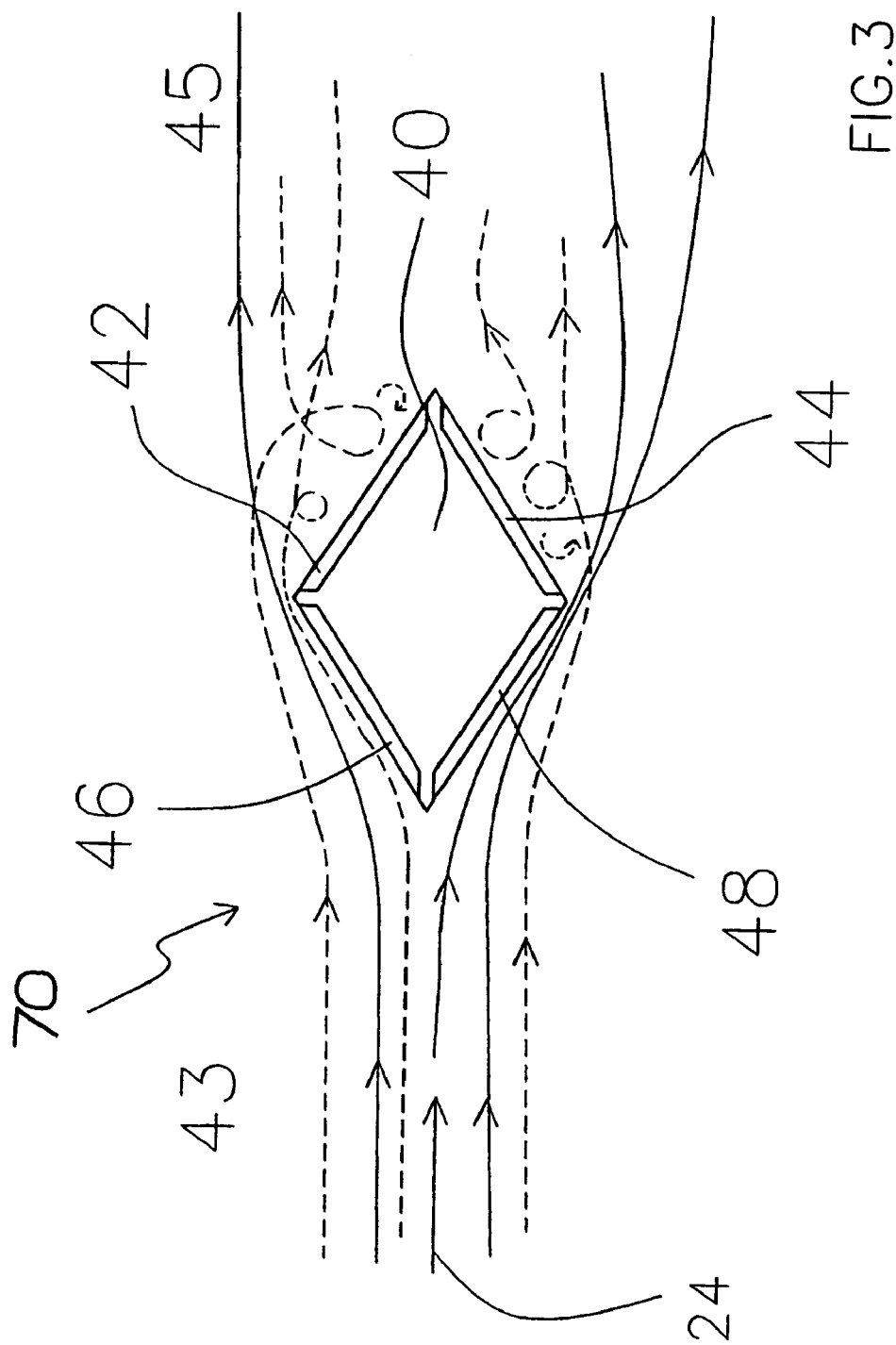
FIG. 3 is an end view of the probe of FIG. 1 showing air flow around the probe and the mechanism for AC current production for medium weight particles and for heavy particles which are further from the probe axis.

FIGS. 2, 5 and 6 show an end view of a probe 40, which is similar to that shown in FIG. 1 with the streamlines of the gas flow 24 depicted in FIGS. 2, 3 and 4 represented by dashed lines. As can be seen, the gas flow remains laminar streaming around the contour of the upstream side 43 of the probe 40 until the point where the gas must make a sudden change in direction to follow the contour of the probe 40. At this point turbulence in the form of vortices or eddies is produced in the gas flow.

As shown in FIG. 2 the heaviest particles will continue to move in a straight line even though the gas flow has diverted to flow around the probe 40. These particles will collide with the electrodes 46, 48 on the upstream side 43 of the probe 40 producing a detector current as described above. However, some particles will follow the streamlines of the gas flow to a sufficient extent to avoid collisions with the probe. FIG. 3 shows the situation that occurs with medium weight particles, which follow the gas flow and are diverted around the probe 40 initially. However, they are too heavy to follow the eddies created on the downstream side 45 of the probe 40 where the gas flow becomes turbulent. Once the particle is no longer entrained in the gas flow it will continue to move generally downstream from the probe 40 in a substantially straight path. Thus the larger particles interact with the electrodes 46, 48 on the upstream side 43 of the probe 40 by inducing a current in the electrodes 46, 48 or by transferring charge by contact with the electrodes 46, 48.

Conversely as shown in FIG. 4, particles of low mass will follow the stream lines of the gas flow and be drawn into the turbulent flow on the downstream side 45 of the probe, bringing the smaller particles within the detection range of the downstream electrodes 42, 44. By having a detector on the downstream side 45 of the probe 40 the probability that lighter particles will be detected is increased.

Advantageously, the probe 40 acts as an air flow deflection means, deflecting the airflow around its contour and causing turbulent flow on its downstream side.

In the embodiment shown in FIGS. 1, 2, 3 and 4 there are four probe electrodes in total, namely electrodes 46, 48 on the upstream side 43 of the probe shaft 40 and electrodes 42, 44 on the downstream side 45 of the probe shaft 40. It is advantageous to have pairs of detectors on the upstream 43 and downstream sides 45 of the probe shaft 40, as it allows the two upstream electrodes 46, 48, and the two downstream electrodes 42, 44 to be coupled differentially to the electronics module of the emission monitoring system to cancel out electrical interference common to both detectors in the pair, such as the electric fields generated by a non-earthed duct or an electrostatic precipitator.

It should be noted that the shape of the probe 40 and the number of electrodes on the surface can be changed to suit the application. The probes of FIGS. 1 to 4 are of square or lozenge shape in cross-section. However FIG. 5 and FIG. 6 illustrate alternative probe cross sections. If desired, a probe can have a single upstream electrode and single downstream electrode, or more than two upstream and two downstream electrodes.

FIGS. 5A to 5E show end views of five additional embodiments of detection means. In each figure the direction of the airflow is shown by arrow 50 and the airflow pattern around the airflow deflection means is shown in broken lines.

FIG. 5A shows an end view of a triboelectric probe 40 with a generally circular cross-section having two detectors 80, 90. The probe 40 is integral with the airflow deflection means.

The airflow pattern around a probe with a circular cross section is dependent on the velocity of the airflow and the size of the probe. Since it will usually be the case that the velocity range for the airflow during normal operation of the equipment on which the probe is installed will be known, the cross sectional size of the probe can be chosen so that vortices are created on the downstream side of the probe. As will be appreciated by the person skilled in the art, the position of vortex separation for a probe with a smoothly curved cross section varies depending on the velocity of the airflow. Therefore, it is preferable to have a corner or some other surface feature on the deflection means, or probe surface, to act as a deflection means, or to have a separate deflection means, to induce vortex separation at a predetermined position. Knowing the position of vortex separation greatly simplifies the task of positioning the detector adjacent to, or in, the turbulent flow.

Returning to FIG. 5A, the upstream detector 80 will detect particles following the laminar airflow as they are deflected around the front part of the probe 40. The downstream detector 90 will detect any particles that are drawn into the vortices on the downstream side 45 of the probe 40.

FIG. 5B shows an end view of a triboelectric probe 40 with a generally rectangular cross section and a detector located on the downstream side 45 of the probe shaft. The probe shaft 40 again acts as the airflow deflection means for this probe. In the probe 40 of FIG. 5B there is no upstream detector, thus only particles light enough to be drawn into the vortices on the downstream side 45 of the probe shaft 40 will be detected by the detector 90. A probe of this configuration may be particularly suited to applications where only particles below a certain size are to be measured.

FIG. 5C shows a detection means including two elongate probes 40, 40A. The first probe shaft 40 has a detector 80 on its upstream face. The first probe 40 acts as an airflow deflection means causing turbulence on its downstream side 45. A second probe shaft 40A is located within the turbulent flow downstream of the first probe shaft 40 and has a detector 90 on its downstream side for detecting small particles entrained in the turbulent flow. The positioning of the downstream detector 90 on the second probe shaft 40A can be chosen to increase the likelihood of interaction with small particles as can the position of the second probe shaft 40A relative to the first probe shaft 40. As discussed above, the upstream detector 80 will tend to detect heavy particles whereas the downstream detector 90 will detect lighter particles.

FIG. 5D illustrates a detection means including two elongate probes 40, 40A and an airflow deflection member 82. The first probe 40 has a detector 80 on its entire surface. This first elongate probe 40 is effectively a standard prior art triboelectric probe. The second probe shaft 40A is placed in the turbulent flow downstream of the airflow deflection member 82 and has two detectors 90 on its surface for detecting particles drawn into the turbulent flow on the downstream of the deflection member 82. The positioning of the downstream detectors 90 on the second probe shaft 40A can be chosen to increase the likelihood of interaction with small particles dependent on the airflow pattern, as can the position of the second probe shaft 40A relative to the airflow deflection means 82. As discussed above, a detector in the laminar flow has greater sensitivity to larger particles whereas the second probe shaft downstream from the deflection means has greater sensitivity to lighter particles.

FIG. 5E shows a triboelectric probe 40 with a generally rhombic or lozenge shaped cross section with a detector 90 located on the downstream side of the probe shaft 40. The shape of probe shaft 40 enables the probe shaft 40 to act as the airflow deflection means for the detector 80. In this embodiment there is no upstream detector thus only particles light enough to be drawn into the vortices on the downstream side of the probe shaft 40 will be detected by the downstream detector 80. A probe of this configuration may be particularly suited to applications where only particles below a certain size are to be measured.

FIGS. 6A to 6J show cross sectional views of a further ten probes according to embodiments of the present invention. The probes in each of the FIGS. 6A to 6J are elongate probes adapted to be placed in a gas flow moving in the direction shown by arrow 50.

In FIGS. 6A to 6J like parts are labeled alike. Each of the probes shown in FIGS. 6A to 6J have two upstream electrodes 46, 48 and two downstream electrodes 42, 44 attached to a probe shaft 40. In these embodiments the probe shaft 40 is also acting as the airflow deflection means with the corners 51, 53 acting as vortex separation means. It will be noted that each of the embodiments of probes shown in FIGS. 6A to 6J are symmetrical about an axis parallel to the direction of gas flow 50. Whilst this feature is not essential to the operation of the system by virtue of the fact that the symmetrical shape of the probe and symmetrical positioning of the upstream and downstream detectors results in approximately equal signals being produces by each of the upstream and each of the downstream detectors, cancellation of interference of the upstream and downstream detectors can more easily be effected when the detectors are connected to the measuring means differentially.

FIG. 6A shows a probe with a square cross section similar to that shown in FIG. 1. The corners 51 and 53 provide a vortex separation means which induce turbulence in the airflow 50 downstream of their position, and in particular, cause turbulent flow adjacent to the downstream detectors 42, 44.

FIG. 6B depicts a probe 40 of rhombic or lozenge shaped cross section. The corners 51 and 53 provide a vortex separation means which induce turbulence downstream of their position, and in particular, cause turbulent flow adjacent to the downstream detectors 42, 44. An elongated shape or streamlined shaped probe can be advantageous in conditions where the abrasive or corrosive nature of the particulate matter causes the probe 40 to be eroded away. The number of particles that collide with the probe 40 are reduced by streamlining the probe and thereby reducing the effect of the particles of the probe 40.

FIG. 6C also depicts a probe 40 of rhombic or lozenge shaped cross section. The corners 51 and 53 provide a vortex separation means which induce turbulence downstream of their position and in particular, cause turbulent flow adjacent to the downstream detectors 42, 44. The relative sharpness of the corners 51 and 53 in comparison to the probe shown in FIG. 6B will cause grater turbulence downstream of their position.

FIG. 6D shows a probe 40 having a generally triangular cross section. The upstream detectors 46, 48 are positioned side by side on the flat front face of the probe shaft 40. The downstream detectors 42, 44 are positioned on respective downstream faces of the probe shaft. Again, the relative sharpness of the corners 51, 53 will cause greater turbulence and can increase the sensitivity of the detector to light particles. Although the upstream detectors 46, 48 are on a single surface it is advantageous to have two separate detectors so that they can be coupled differentially to the measuring means in order to cancel out interference.

FIG. 6E shows a probe 40 having an irregular polygonal shape viewed in cross section, which is symmetrical about an axis lying parallel to the direction of gas flow 50. Each of the upstream faces are of the same length and meet along the axis of symmetry of the probe 40 at a right angle. Each of the downstream faces are of the same length and meet along the axis of symmetry of the probe 40 at an acute angle. The angles of the corners 51 and 53 are equal. In general the geometry of the probe cross section can be chosen to maximize the contact between the downstream detectors 42, 44 and the turbulence created by the corners 51, 53.

FIG. 6F shows a triangular shaped probe 40. The probe cross section is that of an isosceles triangle with its base being on the downstream side of the probe. Thus, the upstream detectors 46, 48 are angled relative to the direction of the gas flow, whereas the downstream face of the probe 40 on which the downstream detectors are mounted lies in a plane perpendicular to the gas flow. The sharp cutoff of the probe 40 at the corners 51, 53 will cause greater turbulence and can increase the sensitivity of the detector to light particles.

FIGS. 6G to 6J show probes 40 with cross sections having curved surfaces. The shape of the curves can be chosen to maximize turbulence produced by the corners 51, 53, or to ensure that the downstream detectors 42, 44 are positioned adjacent to the turbulent flow, or to aid in the deflection of larger particles around the probe in order to reduce collisions and hence probe erosion.

FIG. 6G shows a probe 40 having a cross section of a quadrant of a circle, with the upstream detectors 46, 48 mounted on respective radial sides of the quadrant shape and the down stream detectors 42, 44 being positioned side by side on the circumferential side of the quadrant. The probe of FIG. 6J has the same cross sectional shape as the embodiment of FIG. 6G with the exception that the probe is oriented such that the vertex between the two radial sides of the quadrant shaped cross section lies on the downstream side of the probe 40. Thus the curved surface forms the upstream side of the detector and supports the upstream detectors 46, 48.

The embodiments of probes shown in FIGS. 6H and 6I have two flat faces and two concave surfaces, and are generally diamond shaped in cross section. In FIG. 6H the upstream side faces of the probe 6H are concave whereas in FIG. 6I the downstream faces are concave.

As discussed above the corners 51 and 53 in FIGS. 6A to 6J induce the separation of the gas flow from the contour of the probe and produce turbulent flow downstream of their position, particularly adjacent to the downstream detectors 42, 44. The concave surfaces on the upstream side of FIG. 6H ensures good separation of particles at the corners 51, 53.

The method according to the invention may also be applied to a detection means, which is not an elongate body such as a probe. For example a detector may be mounted on the downstream side of a mass suspended in the gas flow and shaped in an appropriate fashion to cause turbulent flow adjacent to the detector in order to detect light particles in the gas flow. Clearly an upstream detector may also be used with a detection means of this configuration in order to detect larger particle sizes. Application to a ring type detection means is also possible.

The configuration of the detection means depicted in the accompanying figures are merely shown by way of example and are not intended to limit scope of the invention to the configurations depicted.

In the embodiments described above the detectors mounted on the detection means are of the triboelectric type, however the invention is also applicable to detection means utilizing other detector types such as optical detectors.

FIGS. 10A to 10H show a series of configurations of prior art optical emission monitors mounted in a conduit. The block marked 1201 is in each of FIGS. 10A to 10H, a transmitter and the block marked 1202 is in each case, a receiver.

FIG. 10A shows a simple detector with the transmitter 1201 placed diametrically opposite the receiver 1202. Light is transmitted across the conduit 18 through the gas flow to the receiver 1202.

FIG. 10B shows a detector with the transmitter 1201 placed adjacent to a receiver 1202 with a mirror 104 placed diametrically opposite the receiver 1202 and transmitter 1201. Light is transmitted across the conduit through the gas flow to the mirror 104 and reflected back to the receiver 1202. This type of detector provides approximately twice the optical path length of the detector of FIG. 10A meaning that the active detection volume is increased. However, a detector of this sort is more difficult to set up due to the difficulty in aligning the optics and is also difficult to keep contamination free.

FIG. 10C shows a detector with the transmitter 1201 placed adjacent to a receiver 1202 with a prism 106 placed diametrically opposite the receiver 1202 and transmitter 1201. Light is transmitted across the conduit through the gas flow to the prism 106 and reflected back to the receiver 1202. Again this set up has a high active detection volume while being a little easier to set up than the detector described in 10B, however keeping the prism contamination free can also be difficult.

FIG. 10D shows a detector with the transmitter 1201 placed adjacent to a receiver 1202 with a mirror 104 mounted on a mounting means 108 opposite the receiver 1202 and transmitter 1201. Light is transmitted across the conduit through the gas flow to the mirror 104 and reflected back to the receiver 1202. This type of detector can be installed in the conduit 18 as a single article in order to increase the robustness of the detector allowing the alignment of the optics to be fixed in the factory.

FIG. 10E shows a detector with the transmitter 1201 placed adjacent to a receiver 1202 with a prism 106 mounted on a mounting means 108 opposite the receiver 1202 and transmitter 1201. Light is transmitted across the conduit 18 through the gas flow to the prism 106 and reflected back to the receiver 1202. This type of detector can also be installed in the conduit 18 as a single article in order to increase the robustness of the detector. Alignment of the optics is still important but again this can be fixed in the factory.

FIG. 10F shows a detector with the transmitter 1201 placed adjacent to a receiver 1202 with an optic fibre 110 mounted on a mounting means 108 opposite the receiver 1202 and transmitter 1201. The optic fibre or optic fibres 100 are housed within a protective shield. Light is transmitted across the conduit 18 through the gas flow to the optic fibre 110 and then guided back to the receiver 1202. This type of detector can also be installed in the conduit 18 as a single article in order to increase the robustness of the detector. However alignment of the optics is still important.

FIG. 10G shows a detector with the transmitter 1201 placed adjacent to a receiver 1202 with a J shaped optic fibre(s) 100 extending from the receiver 1202. The optic fibre(s) 100 are housed within in a protective shield. Light is transmitted across the conduit 18 through the gas flow to the optic fibre(s) 100 and guided back to the receiver 1202 by the optic fibre(s) 100. This type of detector can also be installed in the conduit 18 as a single article in order to increase the robustness of the detector. Alignment of the optics in this case is simplified, as there is only one air-optics interface to align.

FIG. 10H shows a detector with the transmitter 1201 placed adjacent to a receiver 1202 with J-shaped optic fibres 100 extending from the transmitter 1201. The optic fibres 100 are housed within in a protective shield. Light is guided via the optic fibres to a position in the center of the gas flow, then transmitted through the gas flow to receiver 1202. This type of detector can also be installed in the conduit 18 as a single article in order to increase the robustness of the detector. Alignment of the optics in this case is also simplified, as there is only one air-optics interface to align.

Any one of the configurations shown in prior art FIGS. 10A to 10H can be modified or adapted to be an embodiment of the present invention, however the configurations depicted in FIGS. 10G and 10H are preferable as they are mechanically robust and offer features particularly advantageous for the application described herein as will be apparent to a person skilled in this art.

Figure 11:
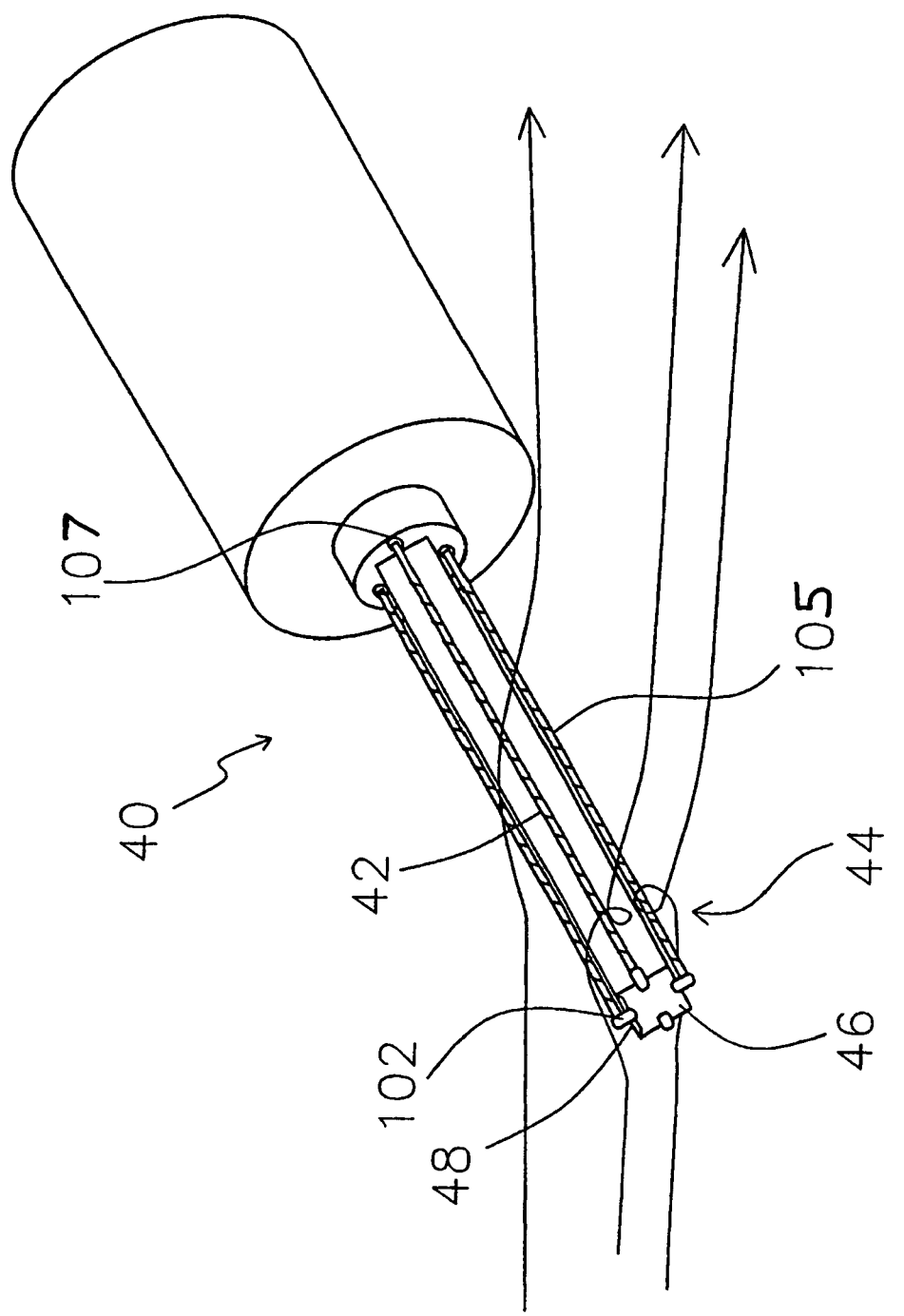
FIG. 11 shows an emission monitor according to an embodiment of the invention having a plurality of optical dynamic opacity detectors.

FIG. 11 shows a detection system using an optical detector of the configuration shown in FIG. 10H combined with the detection means of FIG. 1. Similar to the embodiment shown in FIG. 1 the detection means shown in FIG. 11 has a probe shaft 40 with a rhombic or lozenge shaped cross section. It has two upstream faces 46, 48 and two downstream faces 42, 44 each with associated detectors. The optical fibres, which are acting as light guides for the detectors in this detection system, are housed within the probe shaft 40. A curved elbow portion 102 as shown in FIG. 10H protrudes beyond the probe shaft in order to transmit a beam of light 105 along each face of the probe shaft. Each detector additionally has a receiver 107 mounted on the opposite end of the probe shaft to the curved elbow 102. Thus, the detector produces a light beam substantially parallel to each surface 46, 48, 42, 44 of the probe shaft 40. The downstream detectors will be more likely to detects smaller particles which are entrained in the turbulent flow on the down stream side of the probe shaft 40. Modifications of the optical detection system which are necessary to suit optical dynamic detection of particles, rather than triboelectric detectors, will be known by a person skilled in the art.

In a detection means with multiple optical detectors as shown in FIG. 11 the detectors can share a light source (e.g. a laser diode or other suitable light source, or have one light source for each detector).

It is also possible for the light beam to be shaped so as to increase the likelihood of detecting particles. By shaping the light beam as a ribbon the active detection volume is increased. Furthermore the distance between the probe shaft and the light beam can also be adjusted to ensure detection of the maximum number of particles depending on the probe geometry and velocity of the gas flow.

As discussed above, an effective "closed loop" system can be realized for an optical dynamic detection monitor by modulating the amplitude of the light source, then detecting only that portion of the received signal which is related to that modulation, thus excluding the effect of the interfering signal.

Turning now to the processing of the detector signal(s), the currents induced in the detectors (e.g. 42, 44, 46, 48 of FIG. 1). The detector signal(s) are processed by the electronics module 16 of the emission monitoring system (see FIG. 9). Generally, the electronics module 16 can include either analog or digital signal processing circuitry, therefore in this description unless otherwise stated no distinction will be made between these two possible implementations.

Figure 9:
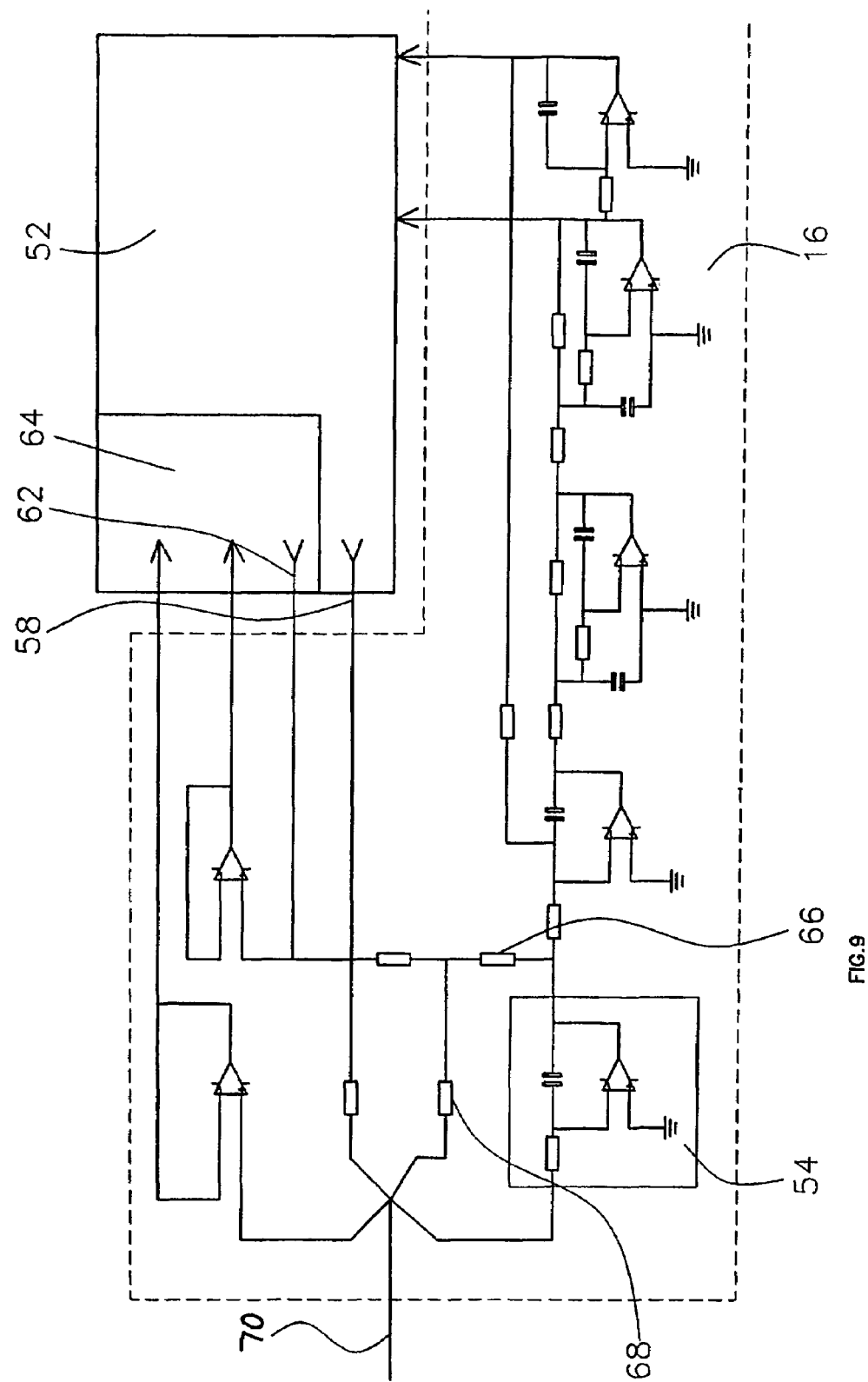
FIG. 9 shows a schematic circuit diagram for an emission monitor according to an embodiment of the present invention.

The electronics module of an emission monitor is shown in FIG. 9 as block 16. In general terms the electronics module contains all electronic and signal processing components of the emission monitor with the exception of the probe itself and the measuring means 52.

The AC component of the signal probe is preferably used for measuring particulate emissions. The DC component is considered unreliable for emission monitoring however it can be used for diagnostic purposes and testing. The chosen cut off frequency between DC and AC frequencies is about 0.1 Hz. However, this can be increased if the velocity of the particles is always high. The upper cut off frequency is limited to below 50 or 60 Hz (as appropriate) in order to avoid interference from the mains power frequency. In most applications the upper cut off frequency of the pass band for the signal processing path of the electronics module is approximately 20 Hz. As will be clear to a person skilled in the art, the upper and lower cut off frequencies of the pass band are chosen by taking into account practical circuitry considerations and possibly the need to restrict total circuit capacitance if the device is to be applied in intrinsically safe situations.

In a digital version the detector signal may be sampled at a rate of 55 Hz, rendering the mains frequency a residual signal at 5 Hz and multiples of 5 Hz. This signal can then be removed using a comb filter that rejects frequencies that are at a harmonic of 5 Hz.

Figure 8:
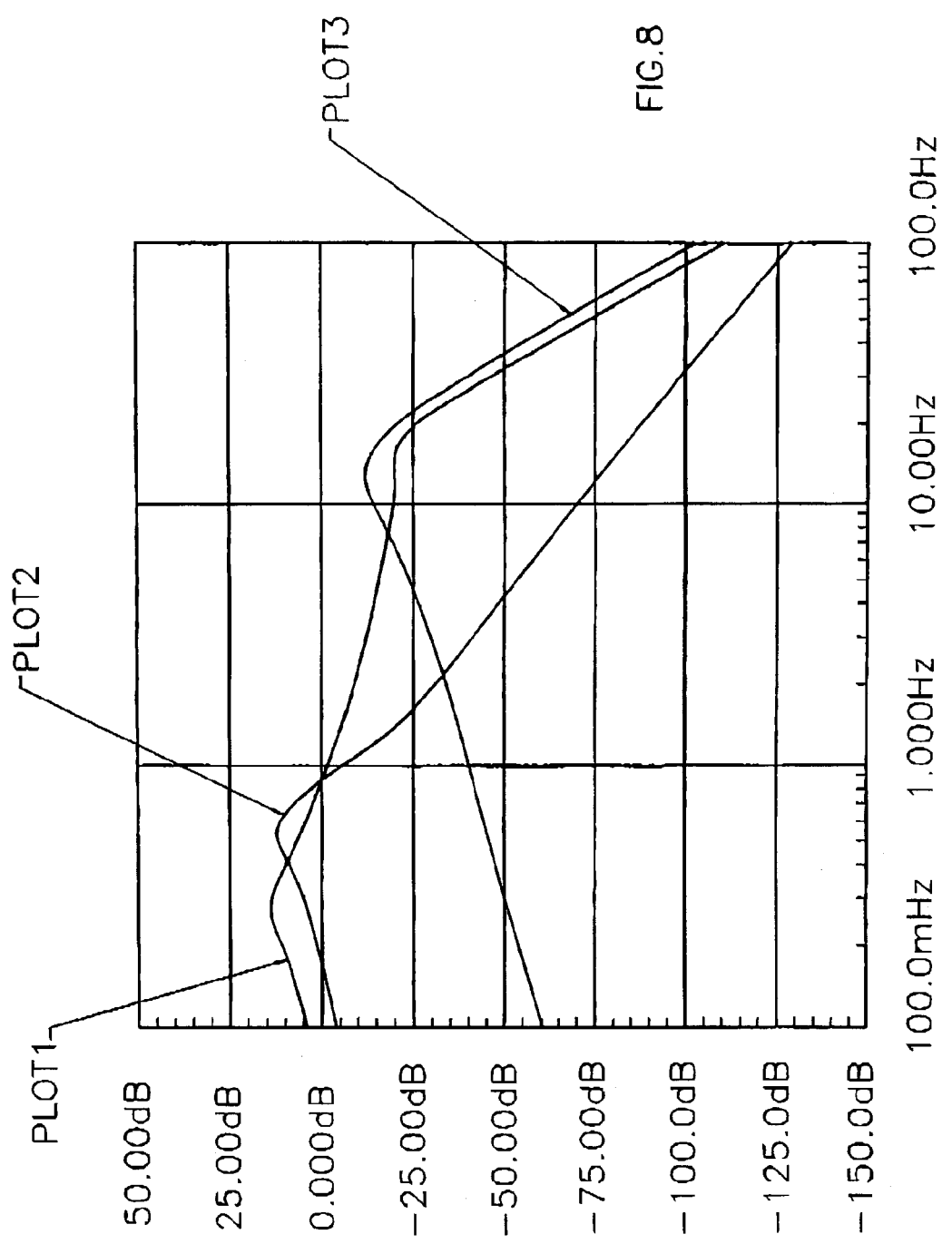
FIG. 8 shows a graph of amplifier gain plotted against frequency, for the frequency response of the integrating pass band of a probe according to an embodiment of the present invention, and also an alternative method using two separate pass-bands.

Integrator 54 is configured to have a frequency response that decreases as the detector signal frequency increases, as shown by plot 1 of FIG. 8. In FIG. 8, the gain of the integrator is plotted against the detector signal frequency on a log scale. In short, the integrator 54 is less sensitive to higher frequencies and more sensitive to lower frequencies.

It can be seen that over a substantial portion of the graph that the frequency response of the integrator is linear with a drop of approximately 6 dB per octave. This is done in order to make the output of the integrator 54 substantially independent of velocity.

If the velocity of the gas flow and particulate material is doubled all mechanical and electrical processes that occur will happen in half the time (i.e. the process of a particle approaching and receding from the probe will take half the time it did at half the velocity). Consequently the duration of the signal produced by each event will be halved and the number of events that occur will double, since the total charge transferred remains the same, the current (which is charge per unit time) will double for any given particle density. Accordingly, the gain of the integrator is reduced in an approximately inversely proportional manner to the amplitude of the detector signal as this frequency changes, rendering the processed signal and hence particle measurement substantially independent of the particle velocity.

In order to partially compensate for frequencies that have been cut off either above or below the pass band of the integrator, an increase in gain is provided for signals near the extreme ends of the pass band.

An alternative method of providing a substantially velocity independent measurement of the density of particles entrained in the gas flow can be performed by splitting the detected signal into a high band and low band detector signal which is then independently processed and smoothed. The ratio of the two values is then used for determining an estimate of velocity by comparison with an empirical relationship. This velocity estimate can then be used to determine the particulate mass concentration as described below. Clearly empirical testing is required in order to determine what ratio of high band to low band frequency relates to a particular velocity of flow.

Plot 2 and 3 of FIG. 8 represent the low band gain and high band gain respectively for an implementation of this method. The low band signal is centered at 1.0 Hz and can be processed by an upward rate limiter to reduce the low band signal sensitivity to interference from low frequency noise caused by, for example, human movement, damper actuation and isokinetic testing, etc. This interference can cause significant energy in the signal at the low frequency end of the pass band that is not directly related to the detector signal. The high band signal is centered at 12 Hz.

As can be seen from FIG. 8, the relationship between the peak gain for the high band and low band signal is approximately inversely proportional to their central frequency. The line joining the peak amplitude points of the two pass bands on a Bode plot would fall at approximately 6 dB per octave which is approximately equal to the response of the integrator in the previous method. In testing it has been found that frequencies above the upper cut off of the low band should be attenuated at approximately 12 decibels per octave more than frequencies below the lower cut off of the high band signal. In order that the high band filter adequately rejects mains interference, it may be designed with higher "Q" (lower damping) than the low band filter.

The ratio between the detected high band signal and detected low band signal are then applied to an empirical function generator to determine an indicated particle velocity. The velocity can then be used to calculate the mass concentration of particulate material in the gas flow as described above. Or alternatively this approach can be combined with the previous method by using the velocity estimate to remove any remaining velocity dependence from the emission measurements.

Alternatively a weighted sum of the high band signal and the low band signal can be used to determine the mass concentration of the particular matter in the gas flow directly.

The key quantities to be measured by an emission monitoring system according to the current embodiment includes, inter alia, the following:

Mass Concentration;
Mass Flow Rate:
Numerical Concentration;
Volume Concentration; and
Class Concentration.

As will be appreciated by a person skilled in the art, Mass Concentration is the most commonly required output in dynamically monitoring airborne industrial discharge, whereas Mass Flow Rate is the most commonly required output in assessing the total airborne discharge from industry over a period of time. Numerical Concentration may be found useful if as expected, future standards place greater importance on smaller particles than present standards. Furthermore Class Concentration provides a numerical particle concentration weighted with particle size so as to match common clean room specification. For example, an output value of 1000 means that the gas stream just meets the particle size distribution specified for class 1000.

Alternatively Volume Concentration may be an alternative to Mass Concentration if particle density is not known.

The other deduced values Gas Velocity, Particle Size and Probe Capacitance are useful for other purposes as described elsewhere.

A process for determining each of these quantities will now be described in which:

Input parameter K is a calibration constant for linearity; K may be adjusted in proportion to relative triboelectric activity of the particulate being measured and reduced to account for any shielding effects;

Input parameter N is the calibration constant for final scaling; N accounts for many factors;

Input parameter D represents the compressed solid particle density in kg/liter, or specific gravity; (a default value of 3 may be used).

Input parameter C is a clean room class factor used to produce weighted output in particles per cubic foot; C is determined by a single test under controlled conditions; and Input parameter A (effective duct area in $m^{2,}$ default 1; may be adjusted to scale True Mass Flow Rate output)

As discussed above, it is advantageous for the detector signal to be proportional to the particle density. As each particle that passes the detector induces a small current in the detector consisting of a negative part and a positive part, when many particles are exposed to the detector at any one time the total signal will be the sum of a number of positive parts and a number of negative parts induced in the detector; this results in a degree of cancellation or masking. As the signals from these particles are essentially unrelated to one another, the sum of the all these individual signals will be a noise signal whose total power is related to the sum of the powers of the constituent signals. As current and voltage are related to the square root of power, the measurement of detector current or voltage will produce a square-root characteristic as shown by plot Y3 in FIG. 7. Mathematically the total signal is said to be the RMS (root mean square) sum of the constituents, which is far smaller than the arithmetic sum of the individual amplitudes.

Figure 7:
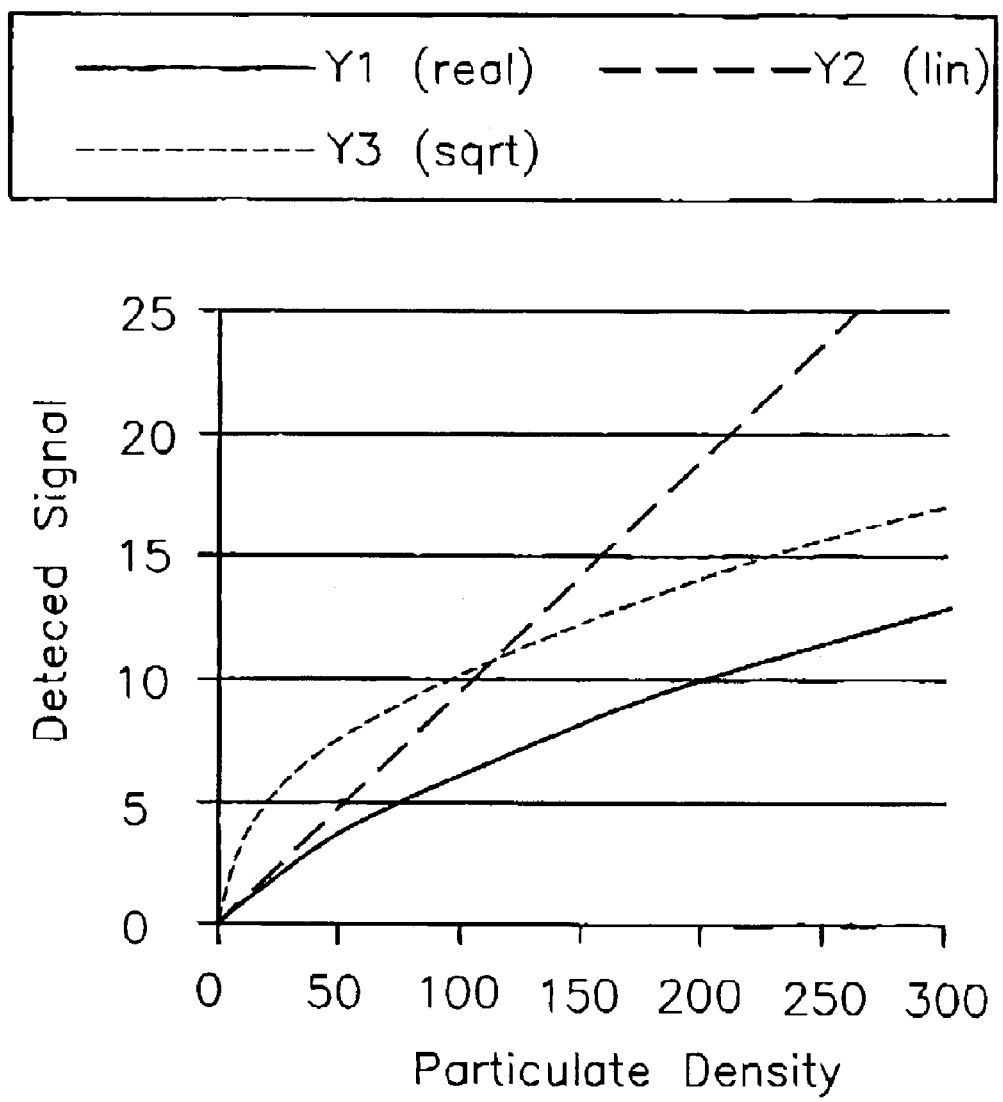
FIG. 7 show a graph of the detector signal versus particulate density for a typical prior art triboelectric probe, and also a model linear probe output.

If the numerical concentration of particles in the gas stream is low enough so that only one particle is detected at a time, there is no cancellation and the detected signal at the measurement means is linearly related to the average particulate mass concentration, as shown in plot Y2 of FIG. 7. In any real measurement the characteristic will vary from that of Y2 at very low signals to that of Y3 at very high signals as shown by plot Y1 in FIG. 7.

In practice, observations on test facilities have indicated that for a 10:1 increase in particulate concentration there will be observed an increase in detected signal commonly between 5:1 and 7:1. By way of comparison, a 10:1 increase in particulate concentration would cause an increase in detected signal of 10:1 if the system were linear (Y2 in FIG. 7), or 3.16:1 if the system were true square root (Y3 in FIG. 7). Since the observed non-linearity is clearly in the transition region between these two extremes, the non linearity characteristic could move towards one extreme or the other as the number of particles exposed to the detector varies. Therefore in order to achieve linearity, an indicator of the number of particles exposed to the detector is found and used to linearise the detector signal rather than assuming a fixed characteristic for this non-linearity correction.

If a particle detection system includes means to measure gas velocity, mean particle size and probe capacitance as proposed elsewhere, then those various signals may also be used to provide the means to deduce the number of particles exposed to the detector, and thence to correct for linearity errors. If any one or more of these signals is not available, then a nominal or estimated constant may be substituted e.g. two methods of measuring gas velocity are described below.

In determining the number of particles exposed to the detector, Probe Capacitance is used as an indication of the effective volume around the probe in which particles can be detected since the two are related to a sufficient accuracy for these purposes. In the calibration of Probe Capacitance, the reference (zero) condition should include any inactive portion of the probe. For example, if the probe projects through a tunnel to the duct, then the reference measurement should be made with a short probe attached that projects through the tunnel just to the duct, but no further. The use of this parameter in the calculation may provide the important benefit of automatically adapting to different probes without otherwise recalibrating, even for reasons such as probe breakage, erosion or high buildup.

In order to determine the quantities of interest, the following calculations can be performed:

Measure Concentration, Gas Velocity, Particle Size and Probe Capacitance as detailed elsewhere.

Convert Concentration into Concentration A by using Gas Velocity and Particle Size to remove dependency on Gas Velocity or Particle Size, as detailed elsewhere.

Calculate Particle Volume=ParticleSize$^3$.

Calculate Concentration B=Concentration A*Probe Capacitance/Particle Volume.

Calculate Concentration C=Concentration B/K.

Calculate Numerical Concentration=Concentration C*(1+Concentration C)*N/Probe Capacitance (or other relationship which generally reverses the nonlinearity of FIG. 7 plot Y1.)

Calculate Volume Concentration=Numerical Concentration*Particle Volume.

Calculate Class Concentration=Volume Concentration*C*Particle Size$^{-0.8}$.

Calculate Mass Concentration=Volume Concentration*D.

Calculate Mass Flow Rate=Mass Concentration*Gas Velocity*A.

Clearly A and D should be adjusted to suit the application. K, N and C may be set initially to any values which suit the system used but subsequently will be set to specific installation default values. Finding the default value of K requires two initial isokinetic tests at substantially different concentrations. Preferably this is performed with minimal variation in the other parameters so that any residual dependencies on those other parameters will not influence the calibration. After such calibration, K will become fixed for that particulate material and conditions. A further simple individual test may be carried out to determine the values of the scaling factors N and C.

The accuracy of all these calculations is preferably (but need not be) better than one percent. However, as the dynamic range required may be very large, it may be more convenient to represent all values in logarithmic form. Logarithmic representation of such values additionally has the benefit of allowing faster execution on smaller processors which may lack a multiply facility, since the simple addition of logarithmic values is equivalent to a multiplication operation.

In any given application, individual on-site isokinetic testing can still further improve accuracy by fine adjustment of K, particularly if conditions are not optimal. By recording the results of all such individual on-site testing, a database of K values will eventually be compiled for all relevant dust materials in various forms and conditions, for example in turbulence, or after an electrostatic precipitator or wet scrubber. It is clear from the foregoing that any attempt made in the past to compile such a database would be severely flawed if it failed to account for these factors.

An exemplary initial calibration process is as follows:

Run the plant on which the emission monitor is mounted with a high particulate mass concentration. Once the flow has stabilized the first of the isokinetic tests used to calculate K as described above can be run.

Average Concentration B as Conc 1 and simultaneously accumulate a sample isokinetically; at the end of Test 1, determine from that sample the total average mass concentration Iso1.

Run the plant with a low particulate mass concentration. Once the flow has stabilized run, Test 2 as described above, averaging Concentration B as Conc2 and simultaneously accumulating a sample isokinetically. At the end of Test 2, determine from that sample the total average mass concentration Iso2.

Calculate $G=Conc\ 2*Iso\ 1/(Conc\ 1*Iso\ 2)$

G represents the required additional gain increase over the tested range to make the detector output linear.

Calculate K for that material and those conditions using:

(Conc 1−G*Conc 2)/(G−1).

A new isokinetic test at any typical concentration under the same conditions can be conducted to determine values of N and C such as to rescale the Mass Concentration and Class Concentration outputs to their correct values. These values need not be further adjusted and they can then be fixed for that implementation of the system.

If the invention is equipped with a serial data interface such as a network port. then all these deduced values may be made available in registers. If only a 4–20 mA interface is provided then only one value may be available at any one time.

In order to check that the signal processing means of the electronics module 16 is functioning correctly, a validation signal can also be applied to the probe via input 58 (FIG. 9). The validation signal is an AC signal with a frequency that lies within the pass band of the signal processing means. The validation signal is combined with the detector signal and processed by the signal processing means simultaneously.

As the validation signal is at a known frequency, it can be filtered out using an appropriate narrow band filter and analyzed separately to the detector signal. For example, the validation signal is generated at 10 Hz and once processed can be removed from the detector signal using a filter.

In the digital version above, the comb filter used to remove mains frequency from the signal will also remove the validation signal from the measurement signal if a 10 Hz validation signal is used. As already discussed, the combined detector and validation signal are sampled at a frequency of 55 Hz thus leaving the validation signal and mains frequency noise as a residual signal at either 5 Hz or a harmonic of 5 Hz. It is also possible to apply a comb filter to the detector signal to separate the measurement signal from the validation signal and the mains interference to obtain further diagnostic information about the functioning of the emission monitor. It will be clear to the person skilled in the art that due to the nature of the detector signal, an insignificant amount of the measurement signal is lost by filtering out the validation signal and mains interference.

The processed validation signal once separated from the measurement signal can then be compared to a reference signal. The reference signal is produced by applying the validation signal to the signal processing means via input 58 during calibration of the instrument (i.e. not under normal operating conditions), and measuring the processed signal produced at the input to the measurement means. The processed reference signal provides an indication of the operation of the signal processing path on the known reference signal under known conditions. This signal is compared to the processed validation signal under normal operating conditions in order to detect any variations in the operation of the signal processing means. The comparison may be carried out by the measurement means, or if one is available, a data acquisition system or the SCADA system attached to the emission monitoring system. If a data acquisition system or the SCADA system is used, a profile of the operation of the apparatus can be built up over time, which can assist in the validation of the emission monitoring system.

Additional information can be gained about the operation of the probe using the DC component of the detector signal. It has been observed that under some conditions, for example when moisture bridges across the insulation between probe and duct, the DC component of the detector current may rise substantially with reference to the AC component. The ratio of the DC component to the AC component can therefore be calculated and compared with a threshold value. When this ratio exceeds the threshold, an alarm may be raised to indicate abnormal process conditions.

A further diagnostic feature can also be provided for a triboelectric emission monitor of this sort. A known electrical excitation signal, known as an admittance measuring signal 62 can be applied to the detectors, and the detector voltage produced, measured by admittance measurement unit 64. The admittance measuring signal should be at a sufficiently high frequency to allow a 1 pF variation in the capacitance of the detector to be easily measured, for example a 40 kHz signal is suitable. The higher the admittance measuring frequency, the more circuit admittance will be tolerable and it may be prudent to use significantly higher frequencies.

In order to detect changes in the admittance of the detector 70 of the previous embodiment, a calibration measurement must be made for a number of known admittances, for example, with no additional admittance attached across the detector and with a single known reference resistor attached across the detector (e.g. a 1 MΩ resistor). The steps taken in calibrating the admittance measuring system are as follows: All calculations and measurements are made in terms of complex (vector) values.

A known complex voltage 62 is applied to the detector with no other impedance attached to the detector 70 and the detector voltage produced is measured. This measurement provides a zero point value for the calculations.

The known impedance is then connected across the detector 70 and the known complex voltage is again applied to the detector 70. The voltage produced from the detector 70 is then measured, thus providing a second reference point for calibration.

The calibration factor Cal for the admittance measurement can now be calculated using the formula:

$$Cal = \frac{1000}{(Yr - Yo)}$$

where $Y_r$ is the complex admittance signal voltage at 62 divided by the complex admittance signal voltage at 70 produced with the 1 MΩ resistor is connected across the detector, $Y_o$ is the complex admittance signal voltage at 62 divided by the complex admittance signal voltage at 70 measured when no connection is made across the detector, and 1000 is the admittance of the 1 MΩ resistor in nS.

Once the $Cal$ value is determined as above, the following formula can be used to calculate the admittance Y of the detector terminal:

$$Y = Cal\ (Y_m - Y_o)$$

wherein $Y_m$, equals the complex admittance signal voltage at 62 divided by the complex admittance signal voltage at 12 and the other quantities are as defined above.

The real part of the admittance measurement signal Y calculated above is a measure of the conductance at the detector and can be used to indicate whether the probe's insulation has been bridged by conductive material and current is either leaking to or from, the conduit.

The imaginary part of the admittance Y can be used as a measurement of the susceptance of the detector or multiplied by 2π.(frequency of the admittance measurement signal) to give a capacitance measurement. The capacitance measurement can be used to determine if the probe's geometry has changed, for example by build up on the probe, breakage or severe bending or the probe, or loss of connection to the probe.

In order to allow emission monitoring and admittance measurement to be conducted simultaneously, it is necessary for the integrator 54 to have a low input impedance at lower frequencies, for example less than 10 kΩ at 1 Hz and a higher input impedance at an input frequency equal to the admittance measuring frequency such as 5 MΩ at 40 kHz. These two preferred characteristics sound contradictory, however the high input impedance at admittance excitation frequency and low impedance over the measurement pass band can be achieved by using an integrator as shown in FIG. 9 by reference numeral 54.

The output of integrator 54 is fed back to the detector via high value resistors 66, 68. At high frequency the integrators gain approaches zero so the input impedance of the detector is defined only by the circuit resistors whereas, at low frequency the input impedance is defined by the following equation:

$$\frac{R_{Feedback}}{1 - Gain_{Integrator}}$$

where $R_{Feedback}$ is the value of the feedback resistor and $Gain_{Integrator}$ the integrator gain. It should be noted that the integrator gain is very high at these frequencies and is negative in value, meaning that the quantity $1-Gain_{Integrator}$ is a large positive value, giving a low impedance at low frequency.

The admittance measuring signal is applied to the detector continuously during normal operation thereby allowing simultaneous measurements of particulate emission and detector parameters. The processing of the admittance signal is undertaken by a separate admittance measurement unit 64.

It should be noted that where in the specification or claims the terms "comprised" or "comprising" are used those terms should be interpreted inclusively rather than exclusively.

It will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention, and modifications obvious to those skilled in the art can be made thereto, without departing from the scope of the present invention.

The invention claimed is:

1. A detection means for detecting particles entrained in a gas stream, said detection means comprising:
    a body adapted to be located in said gas stream and having an upstream face and a downstream face;
    a detector associated with said downstream detection face adapted to detect particles impinging on or passing over said downstream face; and
    said body being shaped and configured to deflect said gas stream around said body in a manner to cause generally turbulent gas flow of said gas stream adjacent said downstream face;
    said detector being adapted to generate a detection signal as a consequence of particles entrained in said turbulent gas flow impinging on or passing over said downstream face.

2. A detection means as claimed in claim 1, wherein said detection signal is used to calculate a detection value that is representative of said particles entrained in said turbulent gas flow.

3. A detection means as claimed in claim 1, wherein said detector is adapted to detect particles impinging on or passing over said upstream face of said body.

4. A detection means as claimed in claim 1, comprising a further detector adapted to detect particles impinging on or passing over said upstream face of said body.

5. A detection means as claimed in claim 1, wherein said at least one detection value includes any one or more of the following detection values for said particles: mass concentration, mass flow rate, numerical concentration, volume concentration, class concentration, or particle size.

6. A detection means as claimed in claim 1, wherein said detector is a triboelectric detector or an optical dynamic opacity detector.

7. A detection means as claimed in claim 1, wherein said body is substantially symmetrical about a plane which lies parallel to the direction of flow of said gas stream.

8. A method of detecting particles moving in a gas stream, said method comprising the steps of:
    (a) introducing a detector means into said gas stream, said detector means including a body having an upstream face and a downstream face, said detector further including a detector associated with said downstream face;
    (b) deflecting said gas stream moving around said body by said body being shaped and configured to thereby cause generally turbulent gas flow of said gas stream adjacent said downstream detection face; and
    (c) generating a detection signal using said detector as said particles entrained in said turbulent gas flow impinge on or pass over said downstream face.

9. A method as claimed in claim 8, wherein said method further includes the step of:
    (d) calculating at least one detection value of said particles in said gas stream from said detection signal generated in step (c).

* * * * *